United States Patent [19]
Karell

[11] Patent Number: 5,509,921
[45] Date of Patent: Apr. 23, 1996

[54] SAFE EAR WAX REMOVER

[76] Inventor: Manuel L. Karell, 3573-22 St., San Francisco, Calif. 94114

[21] Appl. No.: 258,760

[22] Filed: Jun. 13, 1994

Related U.S. Application Data

[63] Continuation-in-part of Ser. No. 153,880, Nov. 17, 1993, Pat. No. 5,334,212.

[51] Int. Cl.⁶ .................................................. A61F 11/00
[52] U.S. Cl. .................................................. 606/162
[58] Field of Search ............................ 606/160, 161, 606/162, 172; 128/864–868, 749

[56] References Cited

U.S. PATENT DOCUMENTS

| | | |
|---|---|---|
| 92,980 | 7/1864 | Lovell . |
| 102,351 | 4/1870 | Wood . |
| 147,660 | 2/1884 | Leiner . |
| 320,889 | 6/1885 | Ruoff . |
| 1,450,612 | 4/1923 | Schultz . |
| 3,099,263 | 7/1963 | Palozzolo . |
| 3,203,418 | 8/1965 | Golinstou . |
| 3,626,946 | 12/1971 | Messeff . |
| 4,227,537 | 10/1980 | Suciu et al. ................ 606/162 |
| 4,411,265 | 10/1983 | Eichenlaub . |
| 5,107,861 | 4/1992 | Narboni . |
| 5,183,461 | 2/1993 | Hobbs . |
| 5,209,757 | 5/1993 | Krug . |
| 5,234,452 | 10/1993 | Wang-Ou . |

FOREIGN PATENT DOCUMENTS

| | | | |
|---|---|---|---|
| 1224482 | 6/1960 | France | 606/162 |
| 0145090 | 7/1902 | Germany | 606/162 |
| 0445257 | 11/1949 | Italy | 606/162 |

*Primary Examiner*—Stephen C. Pellegrino
*Assistant Examiner*—William W. Lewis

[57] ABSTRACT

A Safe Ear Wax Remover is composed of three parts; a wax extractor (26), a safety stopper (10), and an adjuster (30) whereby the three parts combine together making a functional unit. The unit is then placed into the ear canal with stopper resting outside. Once the unit is inserted into the canal, the handle (20) is rotated, wax is caught in the extractor and then the unit is removed from the canal. Wax is thereby safely extracted from the ear canal. Repetitious insertion done, moving the adjuster and stopper to allow increased depth of insertion of extractor, until all wax is extracted. Wax is thereby extracted without visualization of ear drums and thereby can be accomplished by oneself and/or by lay persons.

12 Claims, 6 Drawing Sheets

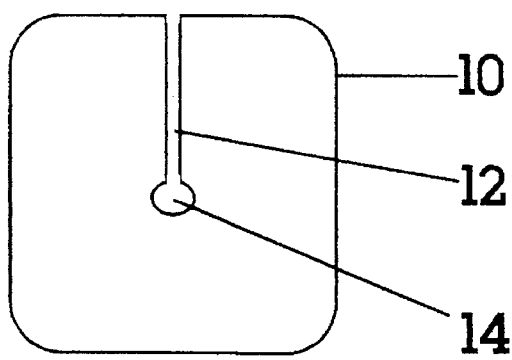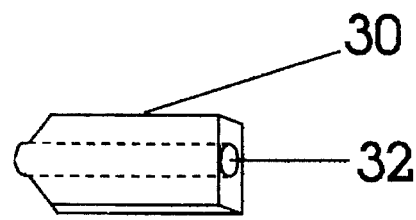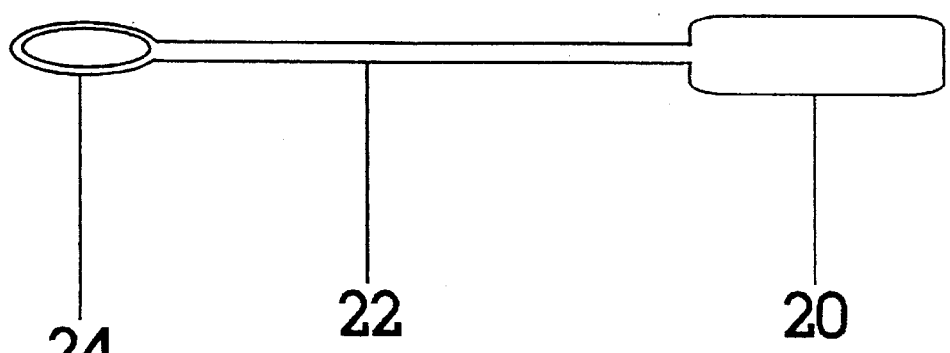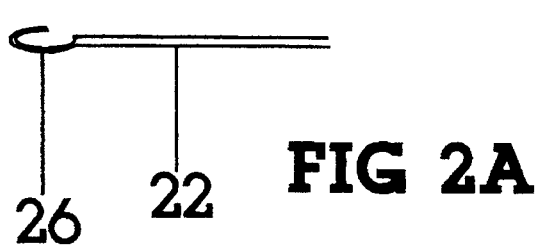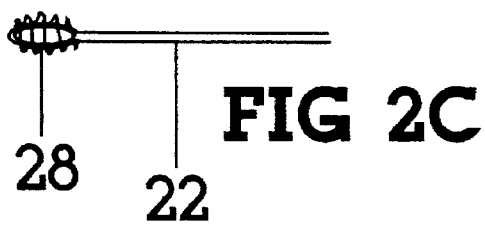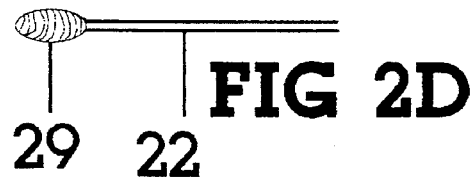

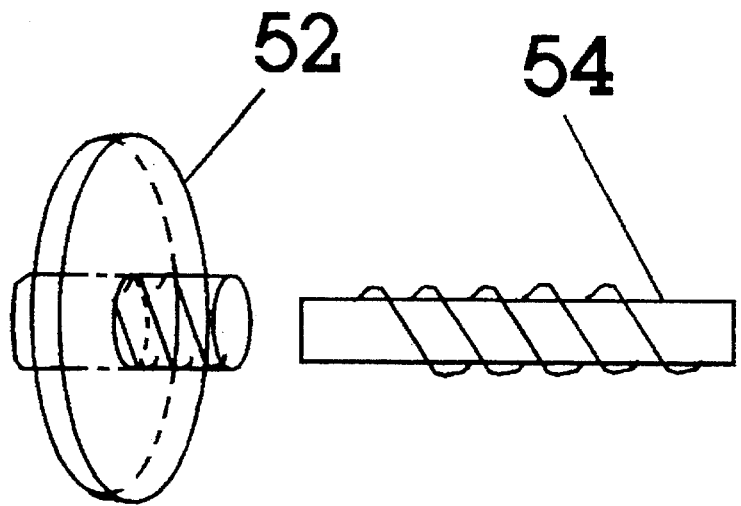
FIG 5A
FIG 5
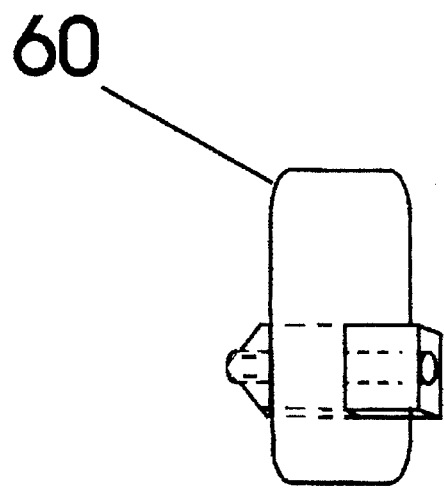
FIG 6

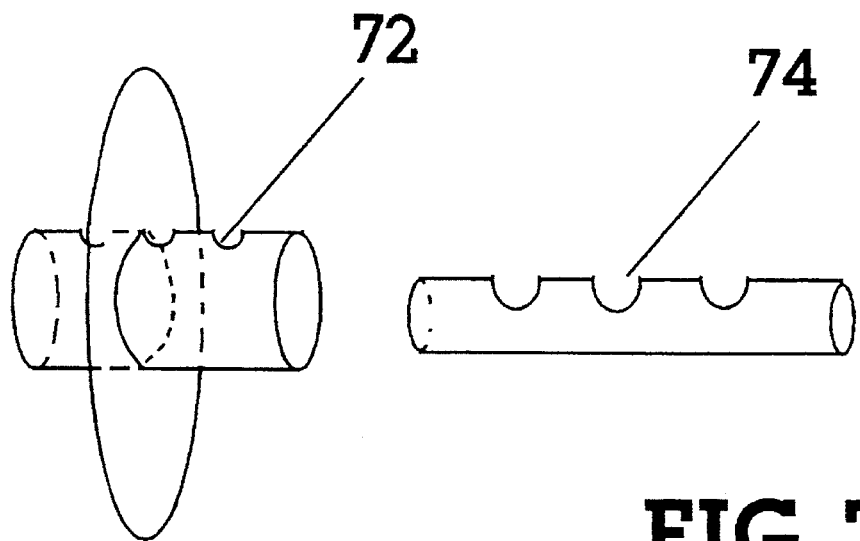
FIG 7  FIG 7A
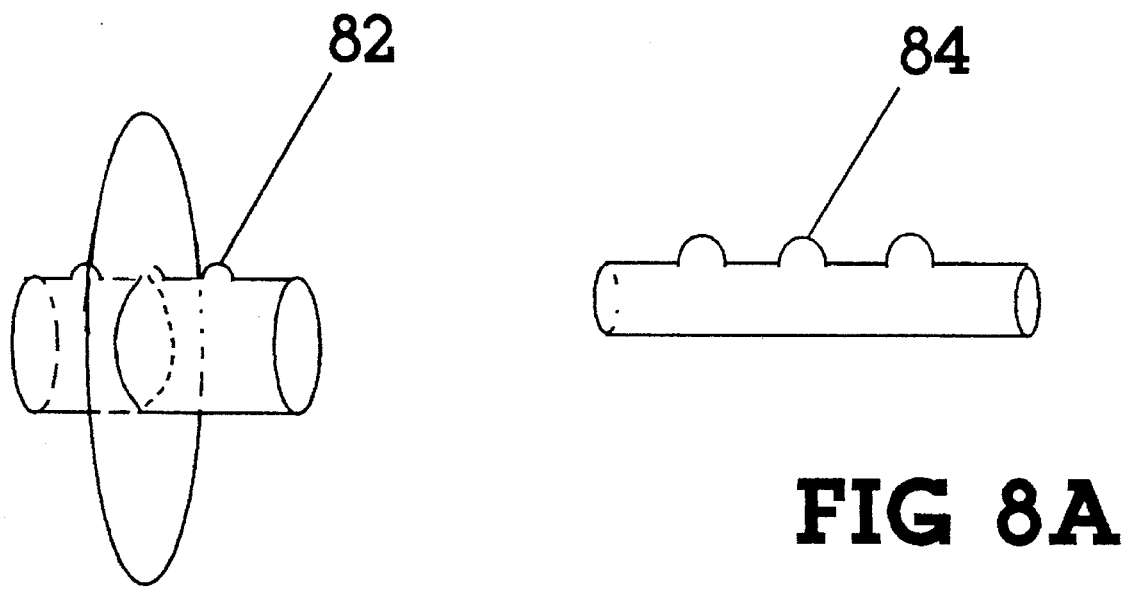
FIG 8  FIG 8A

SAFE EAR WAX REMOVER

This application is a continuation-in-part application to prior U.S. application Ser. No. 08/153,880 filed Nov. 17, 1993 which has since been issued as U.S. Pat. No. 5,334,212 Aug. 2, 1994.

BACKGROUND—FIELD OF INVENTION

The HUMBLE-2 WAX REMOVER™—safe ear wax extractor, generally relates to medical apparatus, and more particularly to a novel apparatus inserted into the ear for the safe removal of ear wax.

BACKGROUND—DESCRIPTION OF PRIOR ART

Ear wax accumulation prevents good hearing and prevents proper hearing aid functioning.

Ear wax also prevents good visualization of the ear drums by health professionals.

Various methods have been used to extract the wax, for example, U.S. 5,107,861 to Narboni, 1992, which uses a ear wax clean button and Pat. No. 5,107,861 to Narboni, 1992, which uses a ear wax clean button and tubular wax collector inserted into the ear. Another apparatus, U.S. Pat. No. 4,411,265 to Eichenlaub, 1979 uses a fluid filled curette to irrigate wax out of the ear. Some physicians use a Water Pik™—dental cleaning device, or a syringe to irrigate the ear and float the wax out of the canal. Other devices used such as U.S. Pat. No. 102,351 to Wood, 1870, uses a brush, and U.S. Pat. No. 3,203,418 to Johnston, 1965, uses a special ear swab. A specially designed ear curette with a wire loop is also used by physicians to manually extract the wax; however, the ear drum has been inadvertently injured in its use.

SUMMARY OF THE INVENTION

The safe ear wax remover is composed of three parts: a wax extractor, a stopper, and an adjuster, whereby the parts are combined making a functional unit, which is then placed into the ear canal. While the stopper mechanism is held tightly against the outer ear, the handle is rotated, wax is caught in the loop and then the unit is extracted from the canal. Wax is thereby safely extracted from the ear canal. Reinsertion is done until all wax is extracted. Readjustment of depth of insertion is accomplished by changing position of the adjuster.

The safe ear wax remover enables the safe extraction of the wax without visualization of the canal or ear drum. It enables lay persons to extract wax from their own ears or from their children's ears.

BRIEF DESCRIPTION OF DRAWINGS

FIG. 1 is a plano drawing of a stopper

FIG. 2 is a plano drawing of a wax extractor with shaft and handle

FIGS. 2A, B, C, D are drawings of different configurations of wax extractors

FIG. 3 is a plano-perspective drawing of an adjuster

FIGS. 5, 5A shows alternative embodiment with shaft and unitary stopper and adjuster having screw and nut arrangement FIG. 6 shows a plano-perspective view of combined unitary stopper and adjuster FIGS. 7, 7A shows a plano view of alternative embodiment having shaft with indentations and unitary stopper and adjuster with protrusions FIGS. 8, 8A shows a plano view of alternative embodiment having a shaft with protrusions and unitary stopper and adjuster with indentations

DETAILED DESCRIPTION OF THE PREFERRED EMBODIMENT

Figure 4:
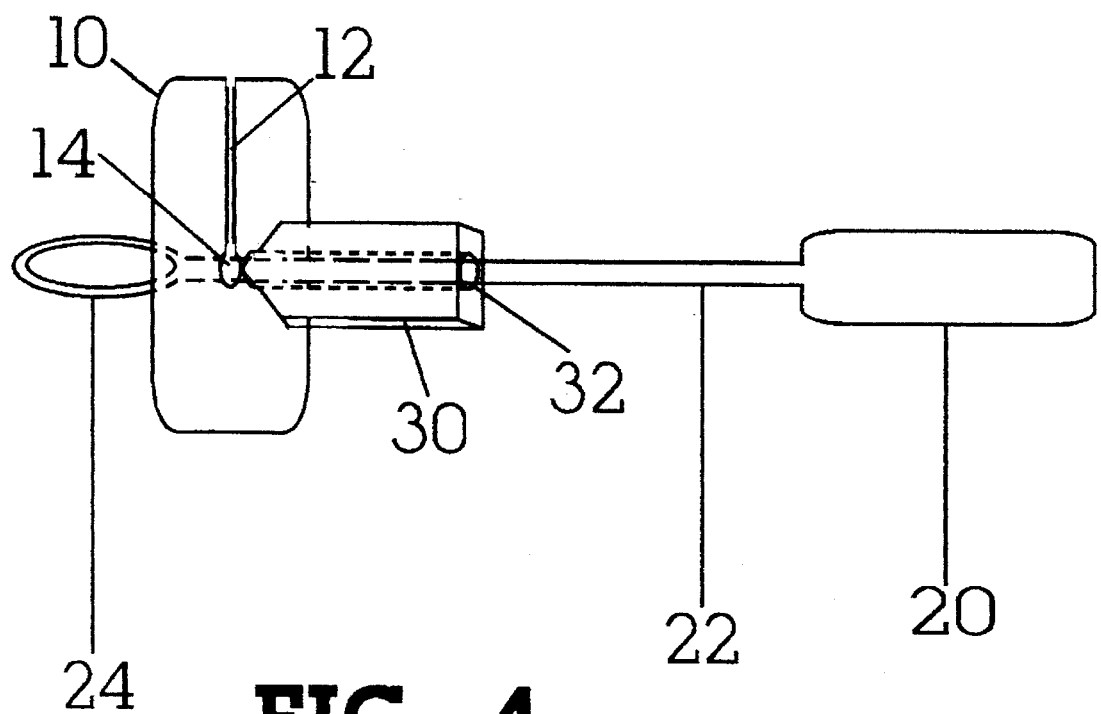
FIGS. 4, 4A are plano-perspective drawings of wax extractor, adjuster making a functional unit
Figure 4A:
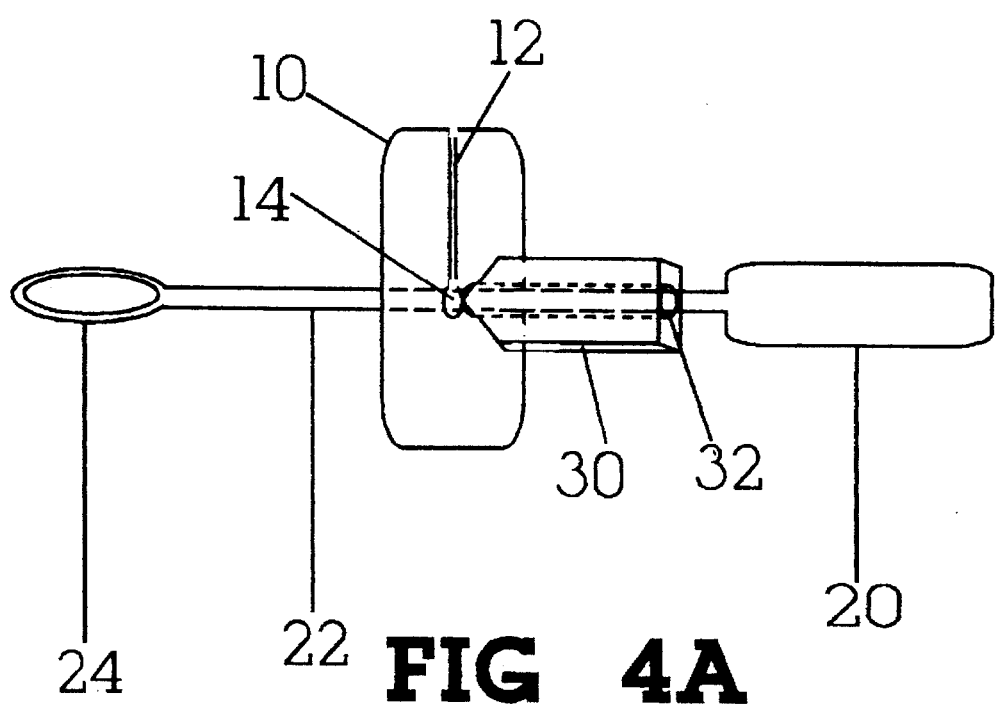
Figure 9:
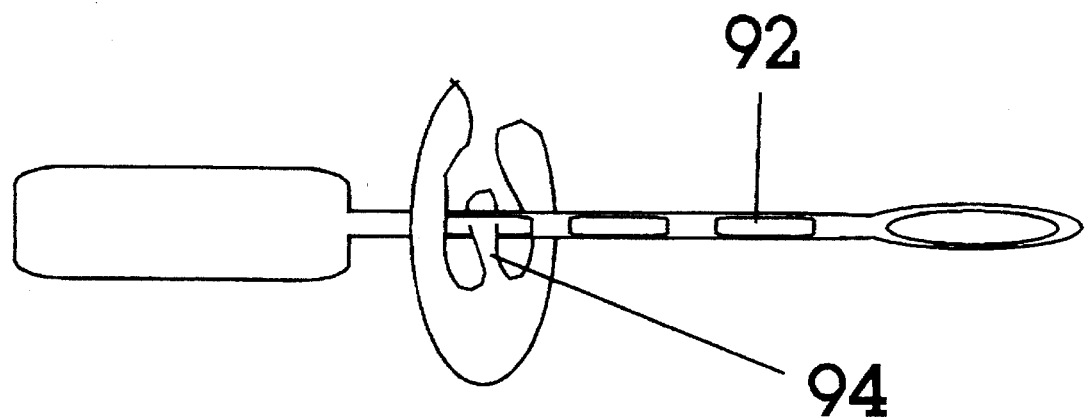
FIG. 9 shows a stopper with rod entering wax extractor shaft hole
Figure 10:
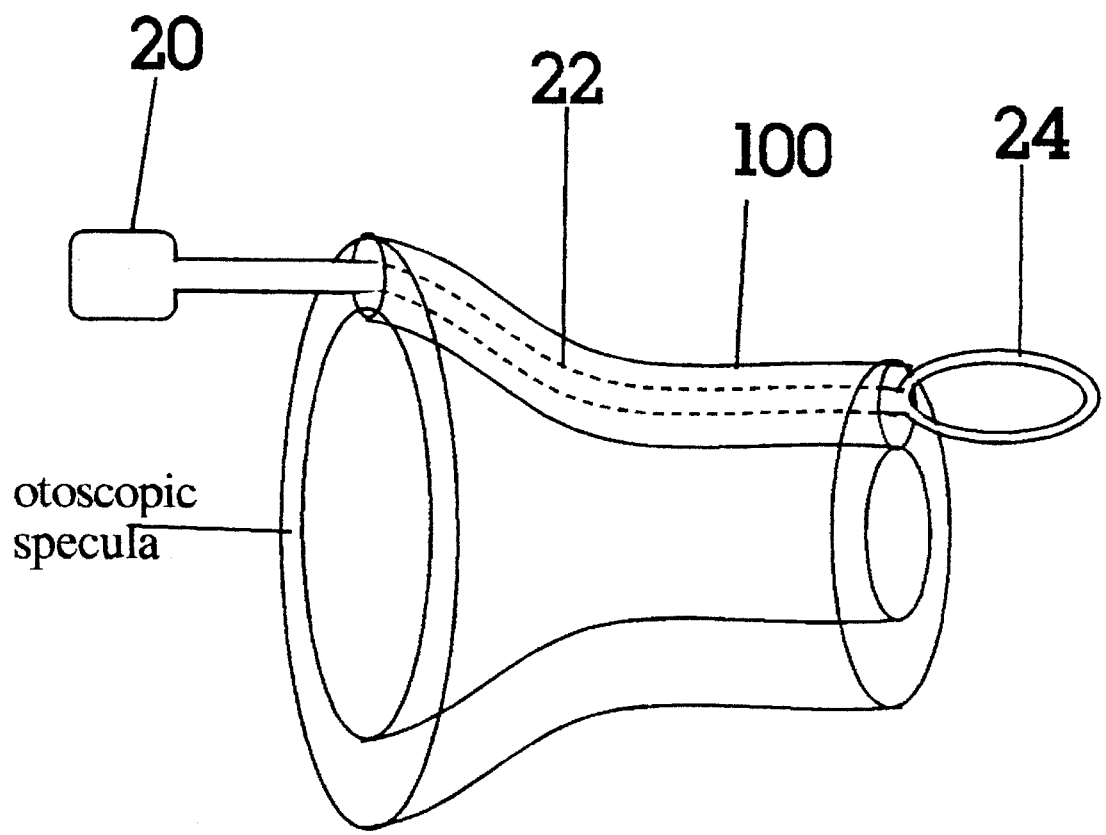
FIG. 10 shows adjustable wax extractor integrally within an otoscopic speculum
Figure 11:
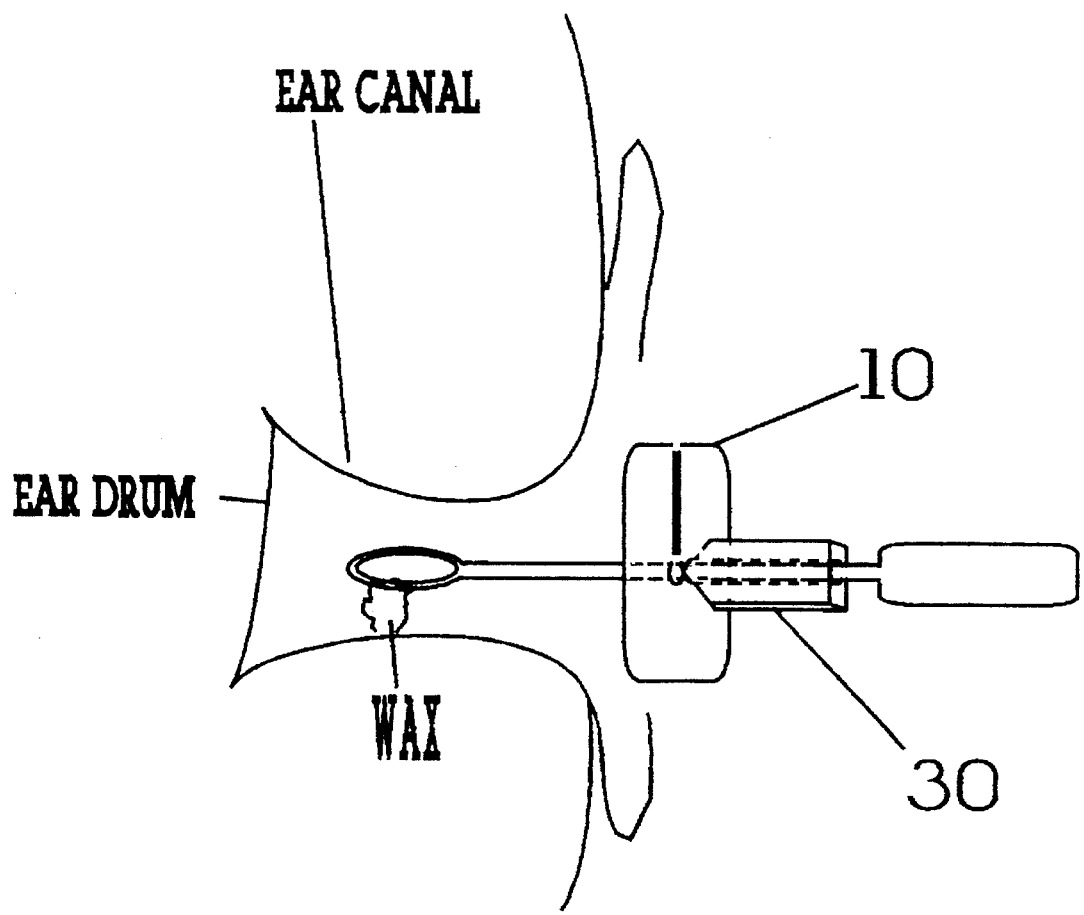
FIG. 11 shows a schematic ear with wax extractor in place

The safe ear wax remover comprises three separate components (FIG. 1, FIG. 2, FIG. 3), which combine together making a functional unit (FIG. 4). FIG. 2 shows a loop curette (24) having a shaft (22) and a handle (20). FIG. 1 shows a stopper (10) having a slit (12) and a central resting hole (14). FIG. 3 shows an adjuster (30) having a central hole (32). In operation, the hole (32) of the adjuster (30) is sufficiently small to create significant friction on the shaft (22), such that it tends to remain in place. The curette (24) is slid into and down the slit (12) of stopper (10) and positioned such that the shaft (22) rests in central resting hole (14). When unit is inserted into the ear canal, the stopper (10) is held tightly against the outer ear, the handle (20) is rotated, wax is caught in the loop and then the unit is extracted from the canal. At first, the adjuster(30) is placed close to curette(24) so that stopper(10) keeps curette(22) depth of insertion shallow. As it is deemed necessary to push curette(24) further into ear canal, the adjuster(30) is moved closer to handle(20), allowing increasing shaft(22) length for ear canal insertion.

Alternative embodiments show details of various wax extractors(26,27,28,29), screw(54) and nut(52) arrangements, combined unitary stopper and adjuster(60), shafts with indentations(74) and protrusions(84), unitary stopper and adjuster with indentations(72) and protrusions(82), shafts with holes(92) and unitary stopper and adjuster with rod(94), and an otoscopic speculum having wax extractor integrally(100) combined.

I claim:

1. An apparatus to remove wax from the ear comprising:
    a shaft having distal and proximal ends, wherein said distal end has a means to extract wax and said proximal end has a handle for manipulation;
    a stopper positioned between distal end and handle, surrounding said shaft and wherein said stopper has a slit ending in a central hole to allow said means to extract wax to be inserted into and through said slit thereby allowing shaft to rest in central hole
    an adjuster, positioned between stopper and handle, slidable, surrounding said shaft and having a hole sufficiently small to cause increased friction onto said shaft, thereby requiring an external force to move adjuster position on shaft; wherein, said means to extract wax, said stopper and said adjuster will act as a functional unit when inserted into the ear canal, preventing said means to extract wax from being inserted too far into the ear canal, thereby preventing ear drum injury as the wax is removed.

2. An apparatus of claim 1 wherein said means to extract wax is a loop curette.

3. An apparatus of claim 1 wherein said means to extract wax is a hook curette.

4. An apparatus of claim 1 wherein said means to extract wax is a spoon curette.

5. An apparatus of claim 1 wherein said means to extract wax is a brush.

6. An apparatus of claim 1 wherein said means to extract wax is a cotton swab.

7. An apparatus of claim 1 wherein said shaft has screw-like protrusions and said adjuster has nut-like indentations.

8. An apparatus of claim 1 wherein said shaft and said adjuster have protrusions and indentations such that shaft and adjuster fit a male/female arrangement.

9. An apparatus of claim 1 wherein said shaft and said adjuster have protrusions and indentations such that shaft and adjuster fit a female/male arrangement.

10. An apparatus of claim 1 wherein said stopper and said adjuster are unitary.

11. An apparatus of claim 1 wherein said shaft has holes; and wherein said stopper and adjuster are unitary; and wherein a rod protrudes into a central hole for fitting into said shaft holes.

12. An apparatus of claim 1 wherein said stopper and adjuster are unitary and shaped into an otoscopic speculum wherein a wall of said otoscopic speculum has a slit and hole for passage of said shaft.

* * * * *